[54] XANTHINE DERIVATIVES

[75] Inventors: Fumio Suzuki, Mishima; Junichi Shimada, Shizuoka; Akira Karasawa, Shizuoka; Hideaki Mizumoto, Shizuoka; Hiroshi Kase, Koganei; Hiromi Nonaka, Shizuoka, all of Japan

[73] Assignee: Kyowa Hakko Kogyo Co., Ltd., Tokyo, Japan

[21] Appl. No.: 29,069

[22] Filed: Mar. 10, 1993

[30] Foreign Application Priority Data

Mar. 12, 1992 [JP] Japan .................................. 4-053385

[51] Int. Cl.$^5$ .................... A61K 31/52; C07D 473/02
[52] U.S. Cl. ................................... 514/263; 544/267; 544/272; 544/273
[58] Field of Search .................. 544/267, 273, 272; 514/263

[56] References Cited

U.S. PATENT DOCUMENTS

| | | | |
|---|---|---|---|
| 4,233,303 | 11/1980 | Bergstrand et al. | 544/273 |
| 4,713,455 | 12/1987 | Furrer et al. | 544/273 |
| 5,068,236 | 11/1991 | Suzuki et al. | 544/273 |

FOREIGN PATENT DOCUMENTS

| | | |
|---|---|---|
| 0369744 | 5/1990 | European Pat. Off. |
| 0389282 | 9/1990 | European Pat. Off. |
| 0415456 | 3/1991 | European Pat. Off. |
| 0501379 | 9/1992 | European Pat. Off. |
| 0386675 | 9/1990 | Japan ............... 544/273 |
| 4346986 | 12/1992 | Japan. |

OTHER PUBLICATIONS

Chemical Abstracts, vol. 108, No. 11 (1988) 945125.
Chemical Abstracts, vol. 109, No. 25 (1988) 221931a.
Chemical Abstracts, vol. 106, No. 19 (1987) 149315w.
Chemical Abstracts, vol. 113, No. 9 (1990) 78009f.

*Primary Examiner*—John M. Ford
*Assistant Examiner*—Payanaram K. Sripada
*Attorney, Agent, or Firm*—Fitzpatrick, Cella, Harper & Scinto

[57] ABSTRACT

A xanthine derivative of the formula (I):

wherein $R^1$ and $R^2$ are the same or different and are substituted or unsubstituted alicyclic alkyl; m1 and m2 are the same or different and represent an integer of 0 to 2; and Q represents (in which $R^3$ and $R^4$ are the same or different and are substituted or unsubstituted alicyclic alkyl) or (in which n is 0 or 1, and Y is a single bond or alkylene); or a pharmaceutically acceptable salt thereof is disclosed.

This derivative has diuretic activity and renal protecting activity.

4 Claims, No Drawings

XANTHINE DERIVATIVES

BACKGROUND OF THE INVENTION

The present invention relates to novel xanthine derivatives. The derivatives are specific antagonists against adenosine $A_1$ receptor which exhibit diuretic activity and renal protecting activity.

Xanthine derivatives have been hitherto known in the prior art. For example, U.S. Pat. No. 5,068,236 (Japanese Published Unexamined Patent Application No. 173888/91) discloses xanthine derivatives of the formula (A):

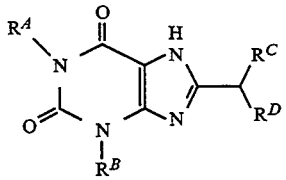

(A)

wherein $R^A$ and $R^B$ are the same or different and are lower alkyl, and $R^C$ and $R^D$ are substituted or unsubstituted alicyclic alkyl. The xanthine derivatives exhibit diuretic activity, renal protecting activity and vasodilator activity.

EP 415456A (Japanese Published Unexamined Patent Application No. 173889/91) discloses xanthine derivatives of the formula (B):

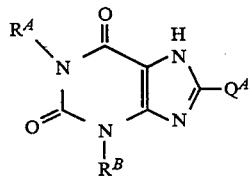

(B)

wherein $R^A$ and $R^B$ are the same as defined above; and $Q^A$ represents

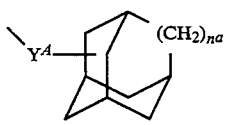

(in which $n^a$ is 0 or 1, and $Y^A$ represents a single bond or alkylene). The xanthine derivatives exhibit diuretic activity, renal protecting activity and bronchodilator activity.

EP 369744A (Japanese Published Unexamined Patent Application No. 178283/90) discloses xanthine derivatives of the formula (C):

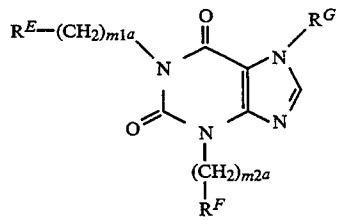

(C)

wherein $R^E$ and $R^F$ are cycloalkyl; $m1^a$ and $m2^a$ are an integer of 0 to 3; and $R^G$ is hydrogen, alkyl, alkenyl, alkynyl, or cycloalkyl. The xanthine derivatives inhibit phosphodiesterases and exhibit cerebro-protective activity.

EP 389282A (Japanese Published Unexamined Patent Application No. 273676/90) discloses xanthine derivatives of the formula (D):

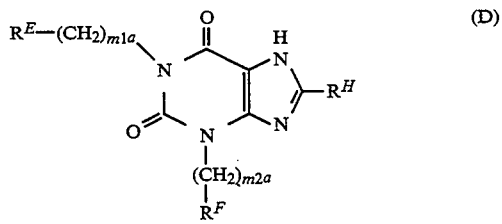

(D)

wherein $R^E$, $R^F$, $m1^a$ and $m2^a$ are the same as defined above; and $R^H$ is halogen, nitro, or

(in which $R^I$ and $R^J$ each independently represent hydrogen, alkyl, or alkylcarbonyl, or $R^I$ and $R^J$ together with the nitrogen to which they are attached form an optionally substituted heterocyclic group). The xanthine derivatives inhibit phosphodiesterases and exhibit antiallergic activity.

SUMMARY OF THE INVENTION

The present invention provides xanthine derivatives represented by the formula (I):

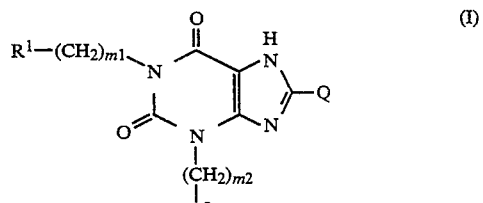

(I)

wherein $R^1$ and $R^2$ are the same or different and are substituted or unsubstituted alicyclic alkyl; m1 and m2 are the same or different and represent an integer of 0 to 2; and Q represents

(in which $R^3$ and $R^4$ are the same or different and are substituted or unsubstituted alicyclic alkyl) or

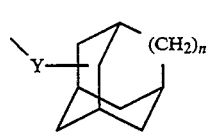

(in which n is 0 or 1, and Y is a single bond or alkylene) and pharmaceutically acceptable salts thereof. The compounds represented by the formula (I) are hereinafter referred to as Compounds (I), and the same applies to the compounds of other formula numbers.

DETAILED DESCRIPTION OF THE INVENTION

In the definitions of the groups in the formula (I), examples of the alicyclic alkyl moiety in the substituted or unsubstituted alicyclic alkyl include cycloalkyl having 3 to 8 carbon atoms such as cyclopropyl, cyclobutyl, cyclopentyl, cyclohexyl, cycloheptyl and cyclooctyl. The alicyclic alkyl may have 1 to 3 substituents and they are the same or different and are, for example, lower alkyl, hydroxy, lower alkoxy, halogen, nitro and amino. Examples of the alkyl moiety in the lower alkyl and the lower alkoxy include straight or branched chain alkyl having 1 to 6 carbon atoms such as methyl, ethyl, propyl, isopropyl, butyl, isobutyl, sec-butyl, tert-butyl, pentyl, neopentyl and hexyl. The halogen includes fluorine, chlorine, bromine and iodine.

Examples of the alkylene include straight or branched chain alkylene having 1 to 4 carbon atoms such as methylene, ethylene, trimethylene, tetramethylene, methylmethylene, propylene and ethylethylene.

The pharmaceutically acceptable salts of Compound (I) include pharmaceutically acceptable acid addition salts, metal salts, ammonium salts, organic amine addition salts and amino acid addition salts.

As the pharmaceutically acceptable acid addition salt, there are salts formed with inorganic acids such as hydrochloride, sulfate and phosphate, and salts formed with organic acids such as acetate, maleate, fumarate, tartrate and citrate. As the metal salt, there are alkali metal salts such as sodium salt and potassium salt, alkaline earth metal salts such as magnesium salt and calcium salt, aluminum salt and zinc salt. As the ammonium salt, there are ammonium salt, tetramethylammonium salt, and the like. As the organic amine addition salt, there are morpholine addition salt, piperidine addition salt, and the like. As the amino acid addition salt, there are lysine addition salt, glycine addition salt, phenylalanine addition salt, and the like.

The process for producing Compounds (I) is described below.

Compounds (I) can be obtained by the following reaction steps.

In the formulae, $R^1$, $R^2$, m1, m2 and Q are the same as defined above.

Step 1

Compound (IV) can be obtained by reaction of Compound (II) (uracil derivative) with Compound (III) (carboxylic acid) or a reactive derivative thereof. Compound (II) can be prepared by a known method (Japanese Published Unexamined Patent Application No. 42383/84).

Examples of the reactive derivative of Compound (III) are acid halides such as acid chloride and acid bromide, active esters such as p-nitrophenyl ester and N-oxysuccinimide, commercially available acid anhydrides, acid anhydrides prepared by using carbodiimide such as 1-ethyl-3-(3-dimethylamino)propylcarbodiimide, diisopropylcarbodiimide or dicyclohexylcarbodiimide, and mixed acid anhydrides with monoethyl carbonate and monoisobutyl carbonate.

When Compound (III) is used, the reaction is carried out by heating to 50° C. to 200° C. in the absence of a solvent.

When the reactive derivative is used, the reaction can be carried out according to a common method in the field of peptide chemistry. For example, the reaction can be carried out in a solvent selected from halogenated hydrocarbons such as methylene chloride, chloroform and dichloroethane, ethers such as dioxane and tetrahydrofuran, dimethylformamide, dimethyl sulfoxide and water. The reaction is carried out at a temperature of −80° C. to 50° C. and is completed within 0.5 to 24 hours. If necessary, the reaction can be carried out in the presence of an additive such as 1-hydroxybenzotriazole or a base such as pyridine, triethylamine, 4-dimethylaminopyridine or N-methylmorpholine. The reactive derivative may be formed in the reaction system and directly used without isolation.

Step 2

Compound (I) can be obtained by ring-closure reaction of Compound (IV) in the presence of a base (Process A), by treatment with a dehydrating agent (Process B), or by heating (Process C).

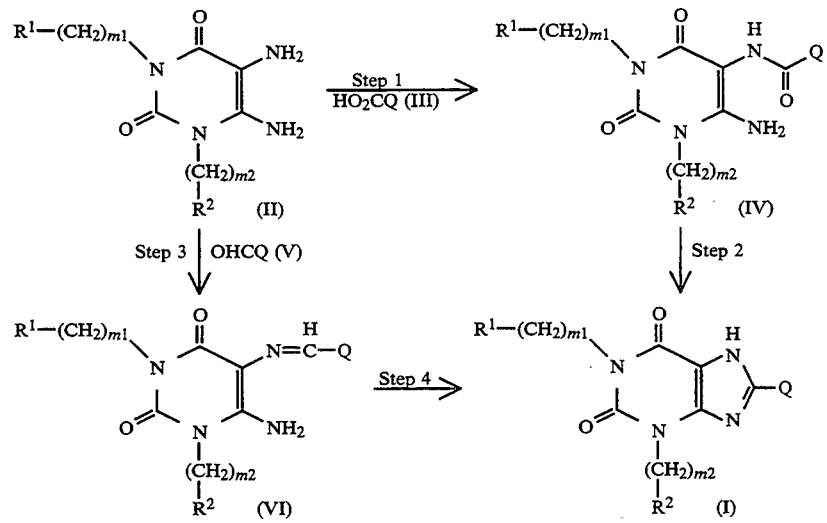

(Process A)

Compound (I) can be obtained by reaction of Compound (IV) in a solvent in the presence of a base at a temperature of 0° C. to 180° C. for 10 minutes to 6 hours.

As the base, alkali metal hydroxides such as sodium hydroxide and potassium hydroxide, and the like may be used. As the solvent, water, lower alcohols such as methanol and ethanol, ethers such as dioxane and tetrahydrofuran, dimethylformamide, dimethyl sulfoxide, and the like may be used alone or in combination.

(Process B)

Compound (I) can be obtained by reaction of Compound (IV) in an inert solvent or in the absence of a solvent in the presence of a dehydrating agent at a temperature of 0° C. to 180° C. for 0.5 to 12 hours.

As the dehydrating agent, thionyl halides such as thionyl chloride, phosphorus oxyhalides such as phosphorus oxychloride, and the like may be used. As the solvent, halogenated hydrocarbons such as methylene chloride, chloroform and dichloroethane, dimethylformamide, dimethyl sulfoxide, and the like may be used.

(Process C)

Compound (I) can be obtained by heating Compound (IV) in a polar solvent at 50° C. to 200° C. for 10 minutes to 5 hours.

As the solvent, dimethylformamide, dimethyl sulfoxide, Dowthermo A (Dow Chemical Co., Ltd.), and the like may be used.

Step 3

Compound (VI) (Schiff base) can be obtained by reaction of Compound (II) with Compound (V) (aldehyde) at a temperature of −20° C. to 100° C. for 0.5 to 12 hours. The reaction is carried out in a solvent such as a mixture of acetic acid and a lower alcohol such as methanol or ethanol.

Step 4

Compound (I) can be obtained by subjecting Compound (VI) to oxidative cyclization reaction. The reaction is carried out at 0° C. to 180° C. for 10 minutes to 12 hours.

As the oxidizing agent, oxygen, ferric chloride, cerium (IV) ammonium nitrate, diethyl azodicarboxylate, etc. may be used. As the solvent, lower alcohols such as methanol and ethanol, halogenated hydrocarbons such as methylene chloride and chloroform, and aromatic hydrocarbons such as toluene, xylene and nitrobenzene, which are inert to the reaction, may be used.

The compounds formed in each of the steps described above can be isolated and purified by a conventional purification method usually employed in the field of synthetic organic chemistry such as filtration, extraction, washing, drying, concentration, recrystallization and various chromatographic processes. The intermediates may be subjected to the subsequent reaction without particular purification.

The salts of Compounds (I) can be obtained by a conventional method usually employed in the field of synthetic organic chemistry. For example, when Compound (I) is obtained in a salt form, it may be purified directly; and when it is obtained in the free form, it is dissolved or suspended in a suitable solvent and an acid or a base is added to the resulting solution or suspension to form a salt.

Compounds (I) and pharmaceutically acceptable salts thereof may form addition products with water or various solvents, and these addition products are also included in the scope of the present invention.

Some of Compounds (I) can exist in the form of optical isomers, and the present invention includes all possible stereoisomers and mixtures thereof.

Examples of Compounds (I) are shown in Table 1.

TABLE 1

| Compound | $R^1$ | $R^2$ | m1 | m2 | Q |
|---|---|---|---|---|---|
| 1 | ▷— | ▷— | 1 | 1 | (noradamantyl) |
| 2 | ▷— | ▷— | 1 | 1 | (bicyclic) |
| 3 | ▷— | ▷— | 0 | 0 | (noradamantyl) |
| 4 | ▷— | ▷— | 0 | 0 | (bicyclic) |

The pharmacological activity of Compounds (I) is illustrated by the following experiments.

Acute toxicity test

Compounds 1, 2 and 3 were orally administered to male dd strain mice (body weight: 20±1 g, 3 mice/group). The mortality was observed 7 days after the administration to determine the minimum lethal dose (MLD).

MLD of the compounds was >300 mg/kg. This is weak toxicity and therefore the compounds can be used safely in a wide dose range.

Adenosine receptor binding test

1) Adenosine $A_1$ receptor binding

This test was conducted according to the method of Bruns et al. [Proc. Natl. Acad. Sci., 77, 5547 (1980)] with slight modification.

Cerebrum of a guinea pig was suspended in ice cooled 50 mM Tris hydroxymethyl aminomethane hydrochloride (Tris HCl) buffer (pH 7.7) by using Polytron homogenizer (manufactured by Kinematicas Co.). The suspension was centrifuged (50,000×g, 10 minutes), and the precipitate was suspended again in the same amount of 50 mM Tris HCl buffer. The suspension was centrifuged under the same conditions, and the precipitate obtained was suspended once again in 50 mM Tris HCl buffer to give a tissue concentration of 100 mg (wet weight)/ml. The tissue suspension was incubated at 37° C. for 30 minutes in the presence of 0.02 unit/mg tissue of adenosine deaminase (manufactured by Sigma Co.). The tissue suspension was then centrifuged (50,000×g, 10 minutes), and 50 mM Tris HCl buffer was added to the precipitate to adjust the concentration of tissue to 10 mg (wet weight)/ml.

To 1 ml of the thus prepared tissue suspension were added 50 μl of cyclohexyladenosine labeled with tritium [$^3$H-CHA, 27 Ci/mmol, manufactured by New England Nuclear Co.] (final concentration: 1.1 nM) and 50 μl of a test compound. The mixture was allowed to stand at 25° C. for 90 minutes and then rapidly filtered by suction through a glass fiber filter (GF/C manufactured by Whatman Co.). The filter was immediately washed three times with 5 ml each of ice cold 50 mM Tris HCl buffer, and transferred to a vial, and a scintillator (EX-H by Wako Pure Chemical Industries, Ltd.) was added thereto. The radioactivity on the filter was determined with a scintillation counter (manufactured by Packard Instrument Co.).

The inhibition rate of the test compound against the binding of $A_1$ receptor ($^3$H-CHA binding) was calculated by the following equation:

$$\text{Inhibition Rate (\%)} = \left(1 - \frac{[B] - [N]}{[T] - [N]}\right) \times 100$$

[Notes]

1. "B" means the radioactivity of $^3$H-CHA bound in the presence of a test compound at a concentration shown in Table 2.
2. "T" means the radioactivity of $^3$H-CHA bound in the absence of a test compound.
3. "N" means the radioactivity of $^3$H-CHA bound in the presence of 10 μM $N^6$-(L-2-phenylisopropyl)adenosine (manufactured by Sigma Co.).

The results are shown in Table 2. The inhibition constant (Ki value) shown in the table was calculated by the Cheng-Prusoff's equation.

2) Adenosine $A_2$ receptor binding test

This test was conducted according to the method of Bruns et al. [Mol. Pharmacol., 29, 331 (1986)] with slight modification.

The similar procedure as in 1) above was repeated using rat corpus striatum to prepare the final precipitate. The precipitate was suspended in 50 mM Tris HCl buffer containing 10 mM magnesium chloride and 0.02 unit/mg tissue of adenosine deaminase (manufactured by Sigma Co.) to give a tissue concentration of 5 mg (wet weight)/ml.

To 1 ml of the thus prepared tissue suspension were added 50 μl of a mixture of N-ethylcarboxamidoadenosine labeled with tritium [$^3$H-NECA, 26 Ci/mmol, manufactured by Amersham Co.] (final concentration: 3.8 nM) and cyclopentyladenosine [CPA, manufactured by Sigma Co.] (final concentration: 50 nM), and 50 μl of a test compound. The mixture was allowed to stand at 25° C. for 120 minutes and then treated in the same manner as in 1) above to determine the radioactivity.

The inhibition rate of the test compound against the binding of $A_2$ receptor ($^3$H-NECA binding) was calculated by the following equation:

$$\text{Inhibition Rate (\%)} = \left(1 - \frac{[B] - [N]}{[T] - [N]}\right) \times 100$$

[Notes]

1. "B" means the radioactivity of $^3$H-NECA bound in the presence of a test compound at a concentration shown in Table 2.
2. "T" means the radioactivity of $^3$H-NECA bound in the absence of a test compound.
3. "N" means the radioactivity of $^3$H-NECA bound in the presence of 100 μM CPA.

The results are shown in Table 2. The Ki value shown in the table was calculated by the following equation:

$$Ki = \frac{IC_{50}}{1 + \frac{L}{Kd} + \frac{C}{Kc}}$$

[Notes]

$IC_{50}$: Concentration at which the inhibition rate is 50%
L: Concentration of $^3$H-NECA
Kd: Dissociation constant of $^3$H-NECA
C: Concentration of CPA
Kc: Inhibition constant of CPA

TABLE 2

| | $A_1$ Receptor | | $A_2$ Receptor | |
|---|---|---|---|---|
| Compound No. | Inhibition (%)/Concentration of Test Compound [$10^{-5}/10^{-4}$ M] | Ki (nM) | Inhibition (%)/Concentration of Test Compound [$10^{-5}/10^{-4}$ M] | Ki (nM) |
| 1 | 99/101 | 1.9 | 49/70 | >10,000 |
| 2 | 100/101 | 2.7 | 93/100 | 210 |
| 3 | 99/98 | 38 | 78/103 | 1,300 |
| 4 | 99/99 | 42 | 104/108 | 2,400 |

Diuretic activity

Male Wistar rats weighing 150 to 300 g were fasted for 18 hours. A test compound and saline (25 ml/kg) were orally administered to the test rats and only saline was administered to the control rats. Then, urine was collected for 6 hours. The test was carried out using 3 groups of animals per test compound, each group consisting of 3 animals. The volume of the urine was measured by using a measuring cylinder and electrolytes ($Na^+$ and $K^+$) in the urine were assayed with a flame photometer (Model 775A manufactured by Hitachi Ltd.).

The results are shown in Table 3.

The parameters in Table 3 are all expressed by relative value to the control.

TABLE 3

| Compound No. | Dose (mg/kg) | Increase in volume of Urine (%) | Increase in Na+ excretion (%) | Increase in K+ excretion (%) | Na+/K+ |
|---|---|---|---|---|---|
| (Control) | — | 0 | 0 | 0 | 1.00 |
| 1 | 0.1 | 184 | 146 | 9 | 2.25 |
| 2 | 1.6 | 43 | 49 | 4 | 1.44 |
| 3 | 1.6 | 93 | 118 | 8 | 2.02 |
|   | 0.1 | 48 | 52 | 0 | 1.52 |
| 4 | 1.6 | 54 | 54 | 18 | 1.31 |
| Amino-phylline[1] | 25 | 34 | 89 | 17 | 1.62 |
| Furose-mide[2] | 25 | 75 | 64 | 57 | 1.07 |

[1] The Merk Index (Eleventh Edition), 1989, page 76
[2] Ditto, page 674

The result indicates that Compound 1 exhibits a potent Na+ diuretic action.

Renal protecting activity (glycerol-induced renal insufficiency model):

Renal insufficiency is the condition that the homeostasis of body fluid is unable to be maintained by disorder of renal function. It is known that subcutaneous or intramuscular administration of glycerol to rat induces acute renal insufficiency characterized by renal tubular disturbance [Can. J. Physiol. Pharmacol., 65, 42 (1987)].

Male Wistar rats were fisted from both food and water for 18 hours. A test compound or saline (control) was intraperitoneally administered to the rats. After 30 minutes, the rats were anesthesized with ether and the back skin was picked up and 0.8 ml/100 g of 50% glycerol was subcutaneously administered. Twenty four hours after the glycerol injection, the rats were anesthesized with ether and 5 ml of the blood was collected from the descending aorta. After being allowed to stand for 30 minutes or longer, the blood sample was centrifuged at 3000 rpm for 10 minutes to obtain the serum. Creatinine in the serum sample was determined using autoanalyzer (AU510, Olympus Optical Co., Ltd.) or clinical analysis kit of creatinine (Creatinine Test Wako; by Wako Pure Chemical Ind., Japan). Urea nitrogen in the serum was determined using autoanalyzer (AU510; made by Olympus Optical Co., Ltd.) or clinical analysis kit of urea nitrogen (Urea Nitrogen Test Wako; by Wako Pure Chemical Ind., Japan).

Further, the left kidneys were taken out from the animals of the test compound-treated groups and the control groups to prepare pathological samples.

The results are shown in Table 4.

TABLE 4

| Compound No. (Dose; mg/Kg) | Creatinine content in serum (mg/dl) | | Urea nitrogen content in serum (mg/dl) | |
|---|---|---|---|---|
| | Control | Test compound administered (significance for control*) | Control | Test compound administered (significance for control*) |
| 1 (0.1) | 4.86 ± 0.12 | 1.97 ± 0.21*** | 152.6 ± 4.1 | 61.3 ± 8.7*** |
| 3 (1) | 4.53 ± 0.19 | 2.23 ± 0.30*** | 193.6 ± 6.4 | 97.2 ± 13.6*** |
| (0.1) | 4.53 ± 0.19 | 2.52 ± 0.24*** | 193.6 ± 6.4 | 109.4 ± 12.8*** |
| 4 (1) | 4.53 ± 0.19 | 2.55 ± 0.43** | 193.6 ± 6.4 | 108.5 ± 16.8** |
| Aminophylline (10) | 5.43 ± 0.11 | 5.32 ± 0.19 | 182.5 ± 3.4 | 174.0 ± 10.4 |
| Furosemide (10) | 3.22 ± 0.35 | 4.17 ± 0.41 | 110.7 ± 9.4 | 150.3 ± 13.7* |
| Normal control | 0.52 ± 0.02 | No glycerol administration | 15.2 ± 0.9 | No glycerol administration |

(*$p < 0.001$, $p < 0.01$, *$p < 0.05$)

Test of the significance between the control group and the test compound-administered group was performed by the Student's t-test (n=8 to 10).

According to the -test results, Compound No. 1 significantly suppressed increases in creatinine content and urea nitrogen content of the serum when intraperitoneally administered at a dose of 0.1 mg/kg ($p<0.001$), whereas aminophylline had a weak effect. On the contrary, furosemide showed a tendency to increase the serum creatinine. The pathological examination of removed kidneys indicates that Compound No. 1 also significantly improved the state of kidneys.

Compounds (I) and pharmaceutically acceptable salts thereof can be used as they are or in various pharmaceutical composition forms.

The pharmaceutical compositions of the present invention can be prepared by uniformly mixing an effective amount of Compound (I) or a pharmaceutically acceptable salt thereof as an active component and a pharmaceutically acceptable carrier. The pharmaceutical compositions are preferably in a unit dose form suitable for oral administration or administration through injection.

For preparing a pharmaceutical composition for oral administration, any useful pharmaceutically acceptable carrier can be used. For example, suspensions and syrups can be prepared using water, sugars such as sucrose, sorbitol and fructose, glycols such as polyethylene glycol and propylene glycol, oils such as sesame oil, olive oil and soybean oil, preservatives such as p-hydroxybenzoic acid esters, flavors such as strawberry flavor and peppermint, and the like. Powders, pills, capsules and tablets can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like. Tablets and capsules are most useful oral unit dose forms because of the readiness of administration. For preparing tablets and capsules, solid pharmaceutical carriers are used.

Injectable preparations can be prepared using a carrier such as distilled water, a salt solution, a glucose solution or a mixture of a salt solution and a glucose solution. The preparations can be prepared in the form of solution, suspension or dispersion according to a conventional method by using a suitable auxiliary.

Compounds (I) and pharmaceutically acceptable salts thereof can be administered orally in the said dosage forms or parenterally as injections. The effective dose and the administration schedule vary depending upon mode of administration, age, body weight and conditions of a patient, etc. However, generally, Compound (I) or a pharmaceutically acceptable salt thereof is administered in a daily dose of 1 to 50 mg/kg in 3 to 4 parts.

Certain embodiments of the invention are illustrated in the following examples.

EXAMPLE 1

1,3-Bis(cyclopropylmethyl)-8-(3-noradamantyl)xanthine (Compound 1)

3-Noradamantane carboxylic acid (1.76 g, 10.6 mmol) was dissolved in 45 ml of pyridine, and 0.84 ml (11.5 mmol) of thionyl chloride was added to the solution under ice cooling. The mixture was stirred at room temperature for one hour and again ice-cooled, and a solution of 2.40 g (9.60 mmol) of Compound b obtained in Reference Example 1 in 45 ml of pyridine was added dropwise to the mixture. The reaction mixture was further stirred at room temperature for one hour and then poured into 300 ml of water. The resulting mixture was extracted three times with 50 ml of chloroform, and the organic layer was washed with a saturated aqueous solution of sodium chloride and dried over anhydrous sodium sulfate. The solvent was evaporated under reduced pressure. The residue was purified by flash chromatography (eluent: 1% methanol/chloroform) to give 3.40 g (yield: 89%) of 6-amino-1,3-bis(cyclopropylmethyl)-5-(noradamantane-3-carbonylamino)uracil (Compound a) as an amorphous substance.

NMR (90 MHz, CDCl$_3$), $\delta$(ppm): 7.46(1H, brs), 5.73(2H, brs), 3.95(2H, d, J=6 Hz), 3.85(2H, d, J=6 Hz), 2.80(1H, t, J=6 Hz), 2.55-1.60(12H, m), 1.45-1.00 (2H, m), 0.70-0.30 (8H, m)

Compound a (3.21 g, 8.07 mmol) was dissolved in a mixture of 45 ml of 2N aqueous solution of sodium hydroxide, 45 ml of dioxane and 10 ml of water, and the solution was heated under reflux for ten minutes. After cooling, the reaction mixture was neutralized with concentrated hydrochloric acid, and extracted three times with 50 ml of chloroform. The organic layer was washed with saturated aqueous solution of sodium chloride and dried over anhydrous sodium sulfate. The solvent was evaporated under reduced pressure, and the crude crystals obtained were recrystallized from ethanol to give 1.87 g (yield: 61%) of Compound 1 as white powder.

Melting point: 210° C.
Elemental analysis (%): C$_{22}$H$_{28}$N$_4$O$_2$ Calcd.: C 69.44, H 7.41, N 14.32 Found: C 69.49, H 7.77, N 14.73
IR (KBr), $\nu_{max}$(cm$^{-1}$): 3176, 2924, 1696, 1658, 1642, 1552, 1497
NMR (270 MHz, CDCl$_3$), $\delta$(ppm): 11.73(1H, brs), 4.04 (2H, d, J=6.9 Hz), 3.97 (2H, d, J=6.9 Hz), 2.81(1H, t, J=6.9 Hz), 2.45-2.35(2H, m), 2.30-2.20(2H, m), 2.10-1.60(8H, m), 1.45-1.20(2H, m), 0.60-0.30(8H, m)
MS (m/e): 380 (M+)

EXAMPLE 2

1,3-Bis(cyclopropylmethyl)-8-dicyclopropylmethylxanthine (Compound 2)

The procedure similar to that described in Example 1 was repeated except that 1.55 g (11.1 mmol) of dicyclopropylacetic acid [Journal of Synthetic Organic Chemistry (Japan), 27, 444 (1969)] and 2.52 g (10.1 mmol) of Compound b obtained in Reference Example 1 were employed in place of 3-noradamantane carboxylic acid and 2.40 g (9.60 mmol) of Compound b, respectively. As a result, 710 mg (yield: 20%) of Compound 2 was obtained as pale yellow powder.

Melting point: 155.0°–155.5° C. (recrystallized from ethanol)
Elemental analysis (%): C$_{20}$H$_{26}$N$_4$O$_2$ Calcd.: C 67.77, H 7.39, N 15.80 Found: C 67.81, H 7.82, N 15.83
IR (KBr), $\nu_{max}$(cm$^{-1}$): 1707, 1643, 1552, 1500
NMR (270 MHz, CDCl$_3$), $\delta$(ppm): 12.56(1H, brs), 4.05(2H, d, J=6.9 Hz), 3.93(2H, d, J=6.9 Hz), 1.75-1.60(1H, m), 1.45-1.25(4H, m), 0.70-0.60(2H, m), 0.60-0.20(14H, m)
MS (m/e): 354 (M+)

EXAMPLE 3

1,3-Dicyclopropyl-8-(3-noradamantyl)xanthine (Compound 3)

The procedure similar to that described in Example 1 was repeated except that 494 mg (2.97 mmol) of 3-noradamantane carboxylic acid and 600 mg (2.70 mmol) of Compound d obtained in Reference Example 2 were employed in place of 1.76 g (10.6 mmol) of 3-noradamantane carboxylic acid and Compound b, respectively. As a result, 380 mg (yield: 40%) of Compound 3 was obtained as white needles.

Melting point: 246.0°–246.5° C. (recrystallized from ethanol/water)
Elemental analysis (%): C$_{20}$H$_{24}$N$_4$O$_2$ Calcd.: C 68.16, H 6.86, N 15.89 Found: C 68.45, H 7.18, N 15.92
IR (KBr), $\nu_{max}$(cm$^{-1}$): 1713, 1662, 1551, 1494
NMR (270 MHz, CDCl$_3$), $\delta$(ppm): 11.50(1H, brs), 3.10-3.00(1H, m), 2.77(1H, t, J=6.9 Hz), 2.70-2.60(1H, m), 2.40-2.20(4H, m), 2.10-1.85(4H, m), 1.85-1.60(4H, m), 1.25-1.05(6H, m), 0.85-0.70(2H, m)
MS (m/e): 352 (M+)

EXAMPLE 4

1,3-Dicyclopropyl-8-dicyclopropylmethylxanthine (Compound 4)

The procedure similar to that described in Example 1 was repeated except that 417 mg (2.97 mmol) of dicyclopropylacetic acid and 600 mg (2.70 mmol) of Compound d obtained in Reference Example 2 were employed in place of 3-noradamantane carboxylic acid and Compound b, respectively. As a result, 270 mg (yield: 24%) of Compound 4 was obtained as light brown powder.

Melting point: 196.8°–198.0° C. (recrystallized from ethanol/water)
Elemental analysis (%): C$_{18}$H$_{22}$N$_4$O$_2$ Calcd.: C 66.23, H 6.79, N 17.16 Found: C 66.01, H 7.01, N 17.10
IR (KBr), $\nu_{max}$(cm$^{-1}$): 1714, 1663, 1553, 1494
NMR (270 MHz, CDCl$_3$), $\delta$(ppm): 12.29(1H, brs), 3.10-3.00(1H, m), 2.65-2.55(1H, m), 1.78(1H, t, J=8.9 Hz), 1.45-1.30(2H, m), 1.20-1.00(6H, m), 0.85-0.75(2H, m), 0.70-0.55(2H, m), 0.45-0.20 (6H, m)

MS (m/e): 326 (M+)

EXAMPLE 5

Tablets

Tablets each having the following composition are prepared in a conventional manner.

| | |
|---|---|
| Compound 1 | 20 mg |
| Lactose | 143.4 mg |
| Potato starch | 30 mg |
| Hydroxypropylcellulose | 6 mg |
| Magnesium stearate | 0.6 mg |

EXAMPLE 6

Granules

Granules having the following composition are prepared in a conventional manner.

| | |
|---|---|
| Compound 3 | 20 mg |
| Lactose | 655 mg |
| Corn starch | 285 mg |
| Hydroxypropylcellulose | 40 mg |

EXAMPLE 7

Capsules

Capsules each having the following composition are prepared in a conventional manner.

| | |
|---|---|
| Compound 1 | 20 mg |
| Avicel | 99.5 mg |
| Magnesium stearate | 0.5 mg |

EXAMPLE 8

Injection

Injection having the following composition is prepared in a conventional manner.

| | |
|---|---|
| Compound 3 | 2 mg |
| Purified soybean oil | 200 mg |
| Purified yolk lecithin | 24 mg |
| Glycerin for injection | 50 mg |
| Distilled water for injection | 1.72 ml |

Reference Example 1

5,6-Diamino-1,3-bis(cyclopropylmethyl) uracil (Compound b)

6-Amino-1,3-bis(cyclopropylmethyl)uracil (1.00 g, 4.26 mmol) (Japanese Published Unexamined Patent Application No. 273676/90) was dissolved in 8 ml of a mixture of ethanol and water (2:1) by heating, and the resulting solution was slowly cooled. After 0.4 ml of concentrated hydrochloric acid was added to the solution at 50° C., 2 ml of aqueous solution of 320 mg (4.68 mmol) of sodium nitrite was added dropwise. The crystals which separated out were collected by filtration and washed with water to give 941 mg (yield: 84%) of 6-amino-1,3-bis(cyclopropylmethyl)-5-nitrosouracil (Compound c) as reddish purple powder.

Melting point: 228°–229° C. (recrystallized from acetonitrile)

Elemental analysis (%): $C_{12}H_{16}N_4O_3$ Calcd.: C 54.54, H 6.10, N 21.20 Found: C 54.83, H 6.03, N 21.20

IR (KBr), $\nu_{max}$(cm$^{-1}$): 1719, 1661, 1585, 1523, 1511

NMR (90 MHz, CDCl$_3$), δ(ppm): 13.20(1H, brs), 9.23(1H, brs), 3.95-3.70(4H, m), 1.45-1.00(2H, m), 0.65-0.30 (8H, m)

MS (m/e): 264 (M+)

Compound c (3.0 g, 11.4 mmol) was suspended in a mixture of 25 ml of water and 40 ml of ethanol. Twenty milliliters of aqueous solution of 6.9 g (40 mmol) of sodium hydrosulfite was added, and the resulting mixture was stirred at room temperature for 2.5 hours. The reaction mixture was extracted three times with 50 ml of chloroform. The organic layer was washed with a saturated aqueous solution of sodium chloride and dried over anhydrous sodium sulfate. The solvent was evaporated under reduced pressure, and the residue was purified by column chromatography (eluent: 3% methanol/chloroform) to give 2.40 g (yield: 84%) of Compound b as an amorphous substance.

NMR (90 MHz, CDCl$_3$), δ(ppm): 5.10(2H, brs), 3.90-3.70(4H, m), 2.30(2H, brs), 1.40-0.95 (2H, m), 0.70-0.30 (8H, m)

MS (m/e): 250 (M+)

Reference Example 2

5,6-Diamino-1,3-dicyclopropyluracil (Compound d)

A mixture of 10.0 g (71.4 mmol) of dicyclopropylurea (Nitrosoureas in Cancer Treatment, INSERM Symposium, 19, 139, 1981) and 6.86 g (80.7 mmol) of cyanoacetic acid was stirred in 20 ml of acetic anhydride at 60° C. for 1.5 hours. Water (100 ml) was added to the reaction mixture, and the resulting mixture was extracted three times with 30 ml of chloroform. The organic layer was washed with a saturated aqueous solution of sodium chloride and dried over anhydrous sodium sulfate. The solvent was evaporated under reduced pressure, and the residue was purified by column chromatography (eluent: 1% methanol/chloroform) to give 11.2 g (yield: 76%) of 1-cyanoacetyl-1,3-dicyclopropylurea (Compound e) as an amorphous substance.

NMR (90 MHz, CDCl$_3$), δ(ppm): 7.65(1H, brs), 3.95(2H, s), 2.90-2.50(2H, m), 1.35-0.45(8H, m)

A solution of 4.80 g (23.2 mmol) of Compound e prepared above and 1.89 g (27.8 mmol) of sodium ethoxide in 100 ml of ethanol was heated under reflux for 20 minutes. After cooling, the reaction mixture was concentrated under reduced pressure to one-third of its original volume and neutralized with concentrated hydrochloric acid. The resulting solution was concentrated under reduced pressure, and the formed crystals were collected by filtration and washed with water to give 1.21 g (yield: 11%) of 6-amino-1,3-dicyclopropyluracil (Compound f) as white powder.

NMR (90 MHz, DMSO-d$_6$), δ—(ppm): 6.63(2H, brs), 4.58(1H, s), 2.70-2.30(2H, m), 1.30-0.45(8H, m)

MS (m/e): 207 (M+)

The procedure similar to that described in Reference Example 1 was repeated except that 1.0 g (4.83 mmol) of Compound f prepared above and 370 mg (5.31 mmol) of sodium nitrite were employed in place of 6-amino-1,3-bis(cyclopropylmethyl)uracil and 320 mg (4.68 mmol) of sodium nitrite, respectively. As a result, 620 mg (yield: 54%) of 6-amino-1,3-dicyclopropyl-5-nitrosouracil (Compound g) was obtained as reddish purple powder.

Melting point: 230° C. (recrystallized from ethanol)

Elemental analysis (%): $C_{10}H_{12}N_4O_3$ Calcd.: C 50.84, H 5.11, N 23.31 Found: C 51.26, H 5.18, N 23.25

IR (KBr), $\nu_{max}(cm^{-1})$: 3200, 1728, 1687, 1628, 1509, 1412

NMR (90 MHz, DMSO-$d_6$), δ(ppm): 13.10(1H, brs), 8.78(1H, brs), 2.75-2.40(2H, m), 1.30-0.50 (8H, m)

MS (m/e): 236 (M+)

The procedure similar to that described in Reference Example 1 was repeated except that 1.55 g (6.57 mmol) of Compound g prepared above and 2.86 g (16.4 mmol) of sodium hydrosulfite were employed in place of 6-amino-1,3-bis(cyclopropylmethyl)uracil and sodium nitrite, respectively. As a result, 1.24 g (yield: 75%) of Compound d was obtained as white powder.

NMR (90 MHz, CDCl$_3$), δ(ppm): 5.23(2H, brs), 2.80-2.50(2H, m), 2.38(2H, brs), 1.40-0.60(8H, m)

MS (m/e): 222 (M+)

What is claimed is:

1. A xanthine derivative of the formula (I):

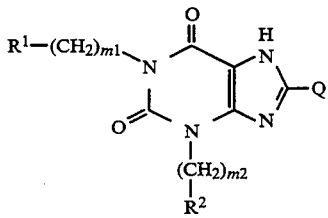

wherein $R^1$ and $R^2$ are the same or different and are alicyclic alkyl which is optionally substituted with one to three substituents independently selected from the group consisting of alkyl having 1-6 carbon atoms, hydroxy, alkoxy having 1-6 carbon atoms, halogen, nitro and amino; m1 and m2 are the same or different and represent an integer of 0 to 2; and Q represents

wherein $R^3$ and $R^4$ are the same or different and are alicyclic alkyl which is optionally substituted with one to three substituents independently selected from the group consisting of alkyl having 1-6 carbon atoms, hydroxy, alkoxy having 1-6 carbon atoms, halogen, nitro and amino, or

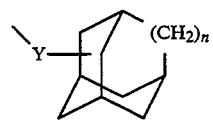

wherein n is 0 or 1 and Y is a single bond or alkylene; or a pharmaceutically acceptable salt thereof.

2. The xanthine compound according to claim 1, wherein $R^1$ and $R^2$ are cyclopropyl.

3. The compound according to claim 1, wherein said salt is selected from the group consisting of acid addition salts, metal salts, ammonium salts, organic amine addition salts and amino acid addition salts.

4. A pharmaceutical composition comprising a pharmaceutically acceptable carrier and as an active ingredient, an effective amount of the derivative as defined by claim 1.

* * * * *

UNITED STATES PATENT AND TRADEMARK OFFICE
CERTIFICATE OF CORRECTION

PATENT NO. : 5,342,841
DATED : August 30, 1994
INVENTOR(S) : FUMIO SUZUKI, ET AL.

Page 1 of 2

It is certified that error appears in the above-identified patent and that said Letters Patent is hereby corrected as shown below:

ON THE TITLE PAGE

At [56] References Cited, FOREIGN PATENT DOCUMENTS
"4346986 12/1992 Japan ." should
read --4-346986 12/1992 Japan .--.
At [56] References Cited, FOREIGN PATENT DOCUMENTS
"0386675 9/1990 Japan ." should
read --386675 9/1990 European Pat. Off. .--.

COLUMN 5

Line 53, "xyiene" should read --xylene--.

COLUMN 9

Table 3, Line 37, "Merk" should read --Merck--.
Line 50, "were fisted" should read --fasted--.
Line 53, "anesthesized" should read --anesthetized--.
Line 55, "Twenty four" should read --Twenty-four--.
Line 57, "sized" should read --tized--.

COLUMN 10

Line 28, "-test" should read --test--.

UNITED STATES PATENT AND TRADEMARK OFFICE
CERTIFICATE OF CORRECTION

PATENT NO. : 5,342,841

DATED : August 30, 1994

INVENTOR(S) : FUMIO SUZUKI, ET AL.

It is certified that error appears in the above-identified patent and that said Letters Patent is hereby corrected as shown below:

COLUMN 14

Line 56, "$\delta$-(ppm):" should read --$\delta$(ppm):--.

Signed and Sealed this

Eleventh Day of April, 1995

Attest:

BRUCE LEHMAN

Attesting Officer    Commissioner of Patents and Trademarks